US012616362B2

(12) United States Patent
Yang

(10) Patent No.: US 12,616,362 B2
(45) Date of Patent: May 5, 2026

(54) MEDICAL ENDOSCOPE WITH SERIALIZER/DESERIALIZER

(71) Applicant: YUAN High-Tech Development Co., Ltd., Taipei (TW)

(72) Inventor: Shih-Huai Yang, Taipei (TW)

(73) Assignee: YUAN High-Tech Development Co., Ltd., Taipei (TW)

( * ) Notice: Subject to any disclaimer, the term of this patent is extended or adjusted under 35 U.S.C. 154(b) by 174 days.

(21) Appl. No.: 18/657,966

(22) Filed: May 8, 2024

(65) Prior Publication Data

US 2024/0285156 A1 Aug. 29, 2024

Related U.S. Application Data

(63) Continuation-in-part of application No. 17/224,257, filed on Apr. 7, 2021, now abandoned.

(30) Foreign Application Priority Data

Dec. 18, 2020 (TW) ................................. 109216801

(51) Int. Cl.
    *A61B 1/05* (2006.01)
    *A61B 1/00* (2006.01)
(52) U.S. Cl.
    CPC .......... *A61B 1/053* (2013.01); *A61B 1/00009* (2013.01); *A61B 1/00018* (2013.01); *A61B 1/00027* (2013.01); *A61B 1/00103* (2013.01)

(58) Field of Classification Search
    CPC . A61B 1/053; A61B 1/00009; A61B 1/00018; A61B 1/00027; A61B 1/00103; A61B 1/00105; A61B 1/00193; A61B 1/00114; H04N 23/555
    See application file for complete search history.

(56) References Cited

U.S. PATENT DOCUMENTS

| | | | | |
|---|---|---|---|---|
| 5,614,943 A * | 3/1997 | Nakamura | ............. | A61B 1/042 |
| | | | | 348/E5.042 |
| 2007/0142703 A1* | 6/2007 | Lu | ......................... | A61B 5/0031 |
| | | | | 600/109 |
| 2010/0198009 A1* | 8/2010 | Farr | ........................ | A61B 90/53 |
| | | | | 600/109 |
| 2010/0298640 A1* | 11/2010 | Oneda | ................ | A61B 1/00105 |
| | | | | 600/109 |
| 2015/0146030 A1* | 5/2015 | Venkataraman | ..... | H04N 13/243 |
| | | | | 348/218.1 |
| 2016/0381278 A1* | 12/2016 | Kang | .................... | H04N 5/265 |
| | | | | 348/68 |

(Continued)

FOREIGN PATENT DOCUMENTS

DE 102013102309 A1 * 9/2013 ............. H04L 25/14

*Primary Examiner* — Anh Tuan T Nguyen
*Assistant Examiner* — Jae Woo
(74) *Attorney, Agent, or Firm* — Demian K. Jackson; Jackson IPG PLLC

(57) ABSTRACT

An apparatus of serializer/deserializer is provided. The apparatus comprises an ISP and capture device at a back end with a disposable image-capture module, a synthetic-image module, and a MIPI serializer at a front end; and, after use, only the disposable image-capture module is discarded, which extends into human body at the front end, but keep the other parts reusable, where cost is thus effectively reduced to solve the shortcoming of high cost of the use of modern disposable endoscope.

8 Claims, 4 Drawing Sheets

(56) References Cited

U.S. PATENT DOCUMENTS

| 2017/0184837 A1* | 6/2017 | Kang ................. A61B 1/00013 |
| 2019/0007647 A1* | 1/2019 | Wen ....................... H04N 7/102 |
| 2021/0112217 A1* | 4/2021 | Jones .................... A61B 1/005 |
| 2023/0190081 A1* | 6/2023 | Schwarz ................ A61B 1/051 |
| | | 600/109 |
| 2025/0204762 A1* | 6/2025 | Viering ............... A61B 1/0676 |

* cited by examiner

MEDICAL ENDOSCOPE WITH SERIALIZER/DESERIALIZER

TECHNICAL FIELD OF THE INVENTION

The present invention relates to an apparatus of medical endoscope using Mobile Industry Processor Interface (MIPI) serializer/deserializer and, more particularly, to discarding a disposable image-capture module only with remaining parts reused, where cost is effectively reduced and the shortcoming of high cost of the use of modern disposable endoscope is solved.

DESCRIPTION OF THE RELATED ARTS

With the advancement of image display technology, medical practices involving the use of endoscopes are becoming more and more widespread. A current medical endoscope device mostly comprises a lens, a light-emitting device, and a hollow tube. After connecting to an external monitor, the image inside a target can be seen.

The medical endoscope is in principle reusable. The host of endoscope along with its mirrors is very expensive. Therefore, after each use, manpower and time must be consumed for cleaning and disinfecting to ensure no infection for next use. However, medical personnel have faced a shortage in recent years. If the post-processing after using the endoscope could be simplified, more convenience would be brought to medical behaviors.

In the existing technical field of medical equipment for solving the problems of insufficient manpower and insufficient cleaning and disinfection, technical concept of discarding is accepted for endoscope. This kind of endoscope has a long tube for inserting into an opening of a body. The inserting tube of the endoscope usually comprises a system of optical fiber and lens for carrying the assembled visual information out of a patient's body; and a light source for illuminating the area to be seen. In the design of this disposable endoscope, the following parts are combined into a single integrated entity: a detector (including a lighting, a photographer, etc.), an image signal processor (ISP), an interface of universal serial bus (USB), etc., where all expensive parts of the disposable endoscope are designed at the front end of the tube and the entire tube with the inserted parts is discarded after use. Yet, this method is expensive due to the high cost of imaging optics. The throwing away after use is not only very wasteful but also inconsistent with economic benefits. Hence, the prior arts do not fulfill all users' requests on actual use.

SUMMARY OF THE INVENTION

The main purpose of the present invention is to set the most expensive ISP and capture device at a back end with a disposable image-capture module, a synthetic-image module, and a MIPI serializer at a front end; and, after use, only discard the disposable image-capture module, which extends into human body at the front end, but keep the other parts reusable, where cost is thus effectively reduced to solve the shortcoming of high cost of the use of modern disposable endoscope.

To achieve the above purposes, the present invention is an apparatus of medical endoscope using MIPI serializer/deserializer, comprising a holding unit and a capture unit, where the holding unit and the capture unit are connected through a coaxial cable, and comprises a disposable image-capture module, a synthetic-image module, a MIPI serializer, a MIPI deserializer, a MIPI capture card, and a capture device; the disposable image-capture module is set at a first end of the holding unit; the disposable image-capture module comprises a left image sensor and a right image sensor; the left image sensor and the right image sensor capture a set of left-image signals and a set of right-image signals, respectively; the set of left-image signals and the set of right-image signals are converted for conforming to a MIPI single-channel (MIPI-1-lane) interface; the synthetic-image module is set in the holding unit and connects to the disposable image-capture module; the synthetic-image module receives the set of left-image signals and the set of right-image signals to form a set of synthesized image signals containing all of the left-image signals and the right-image signals; the set of synthesized image signals are converted for conforming to a MIPI dual-channel (MIPI-2-lane) interface; the MIPI serializer is set in the holding unit and connects to the synthetic-image module; the MIPI serializer MIPI-serializes the set of synthesized image signals for outputting a flow of MIPI-serialized image data to the coaxial cable; the MIPI deserializer is set in the capture unit and connects to the MIPI serializer through the coaxial cable to MIPI-deserialize the flow of MIPI-serialized image data to be restored and conformed to the MIPI-2-lane interface for outputting the set of synthesized image signals; the MIPI capture card is set in the capture unit and connects to the MIPI deserializer for receiving the set of synthesized image signals to be converted into a set of parallel signals; and the capture device is set in the capture unit and connects to the MIPI serializer to receive the set of parallel signals for being converted into a set of video-format data. Accordingly, a novel apparatus of medical endoscope using MIPI serializer/deserializer is obtained.

To achieve the above purposes, the present invention further provides an apparatus of medical endoscope using MIPI serializer/deserializer, comprising:

a holding unit comprising:

a multiple-use guide tube configured for extending into a body;

a single-use image-capture module arranged at a first end of the guide tube, wherein the single-use image-capture module comprises a left image sensor and a right image sensor, wherein said left image sensor and said right image sensor capture a set of left-image signals and a set of right-image signals, respectively, wherein said set of left-image signals and said set of right-image signals are each a single-channel signal;

a multiple-use synthetic-image module disposed in said holding unit, detachably connected to the single-use image-capture module, and receiving said single-channel sets of left-image signals and right-image signals to synthesize a set of dual-channel image signals containing all of said left-image signals and said right-image signals, the dual-channel image signals including differential signal PCLK and differential signal Data; and a multiple-use differential signal serializer disposed in said holding unit and connected to said synthetic-image module, wherein said differential signal serializer includes: a Format Convertor and scramble electrically connected to the synthetic-image module; a parallel to serial electrically connected to the Format Convertor and scramble; a CD (Cable Driver) electrically connected to the parallel to serial; a Low Pass filter electrically connected to the CD; a I2C GPIO Decoder electrically connected to the Low Pass filter; and a PLL and CLK_DIV electrically connected to the synthetic-image module, the Format Convertor and scramble, and the parallel to serial; the synthetic image signal (differential signal PCLK and differential signal Data) entering the differential signal serializer, the PLL and CLK_DIV assisting the Format Convertor and scramble and the parallel to serial in locking a frequency to be processed, the Convertor and scramble converting a format of the synthetic image signal (differential signal PCLK and differential signal Data) and performing encryption thereon through scrambling, serializing the synthetic image signal by the parallel to serial, converting parallel transmission to serial transmission, controlling a transmission channel of the coaxial cable by the CD, allowing the flow of differential signal-serialized image data outputted by the parallel to serial to be transmitted, wherein the flow of differential signal-serialized image data is also inputted to the Low Pass filter to filter out internal high-frequency video signals, allowing internal low-frequency I2C and GPIO to enter the I2C GPIO Decoder for decoding and then sending out low-frequency I2C and GPIO control signal;

a multiple-use capture unit comprising:

a differential signal deserializer disposed in said capture unit and connected to said differential signal serializer, wherein said differential signal deserializer includes: an EQ (Equalizer) electrically connected to the differential signal serializer through the coaxial cable; a CDR (Clock Data Recovery) electrically connected to the EQ; a serial to parallel electrically connected to the CDR; a Descramble and Format Convertor electrically connected to the serial to parallel; a Low Pass filter electrically connected to the EQ; a I2C GPIO Encoder electrically connected to the Low Pass filter; and a PLL and CLK_DIV electrically connected to the CDR, the serial to parallel, and the Descramble and Format Convertor, the PLL and CLK_DIV assisting the serial to parallel and the Descramble and Format Convertor in locking a frequency to be processed, wherein, after I2C and GPIO signal have entered the I2C GPIO Encoder for encoding, the Low Pass filter filters out high-frequency signal, allowing low-frequency I2C and GPIO control signal and the flow of differential signal-serialized image data to pass through the EQ and then enter the CDR to separate Clock and Data, converting serial transmission into parallel transmission by the serial to parallel, allowing the Descramble and Format Convertor to perform descrambling and format conversion, reducing to a dual-channel interface of differential signal Data and differential signal PCLK, finally outputting the synthetic image signal;

a differential signal capture card disposed in said capture unit and connected to said differential signal deserializer, the differential signal capture card comprising an L/R splitter configured to receive the set of synthesized image signals to be split into two sets of image signals conformed to the single-channel signal, wherein the two sets of image signals conformed to the single-channel signal are outputted to an image signal processor (ISP) and converted into two sets of image signals conformed to the dual-channel signal, wherein the two sets of image signals conformed to the dual-channel signal are processed through a parallel data conversion to obtain parallel signals;

a multiple-use coaxial cable connecting the differential signal serializer of the holding unit and the differential signal deserializer of the capture unit; and a multiple-use power-over-cable (PoC) module comprising:

a PoC sending circuit disposed between the coaxial cable and the differential signal deserializer and configured to send power over the coaxial cable; and a PoC receiving circuit disposed between the differential signal serializer and the coaxial cable and configured to receive power from the coaxial cable to supply power to the single-use image-capture module at the first end of the holding unit. The coaxial cable has a length of 2~10 meters.

The differential signal includes MIPI, LVDS, CML.

The differential signal serializer and said differential signal deserializer are constructed in an FPGA.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
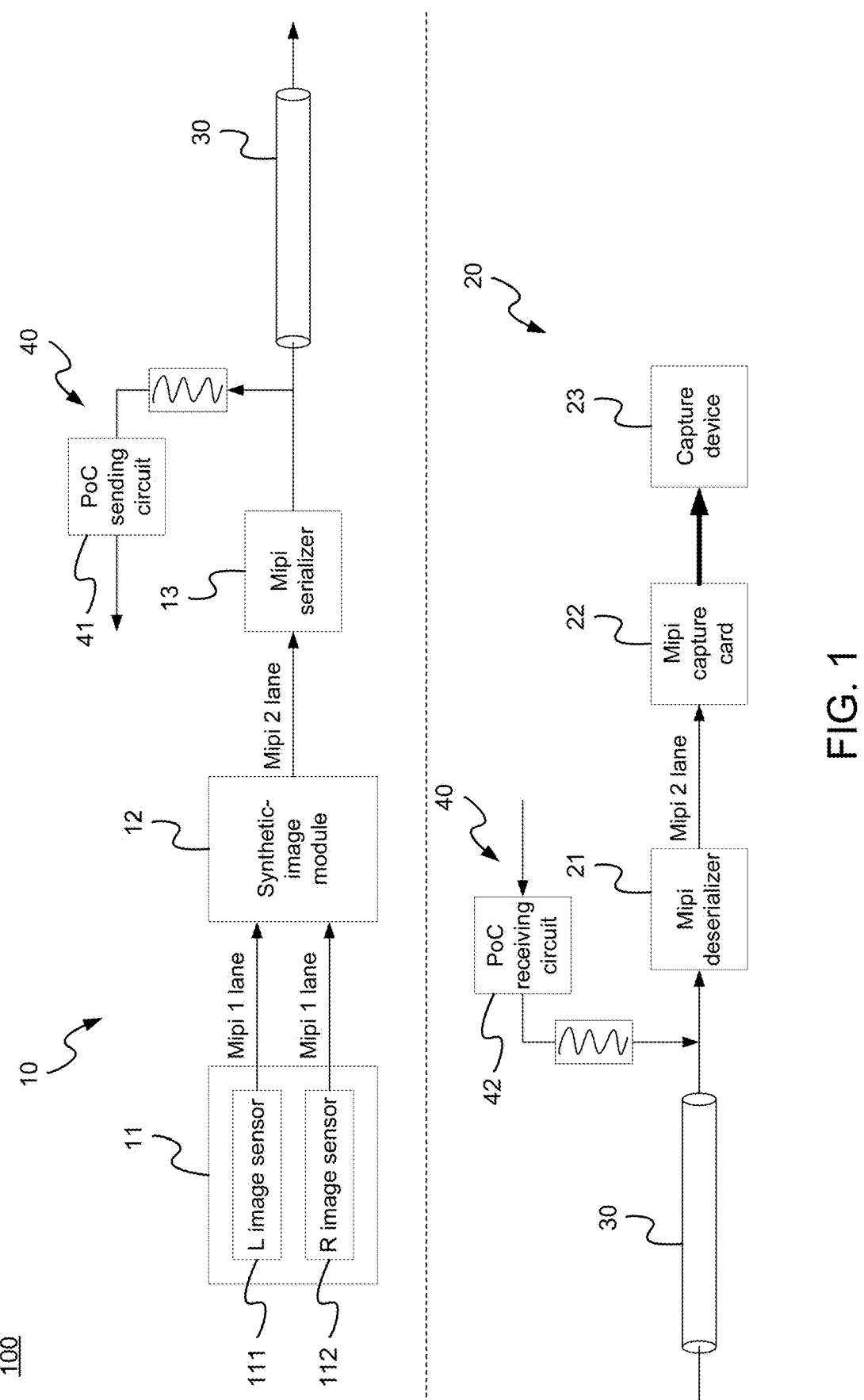
FIG. 1 is a schematic view showing the structure of the preferred embodiment according to the present invention.
Figure 2:
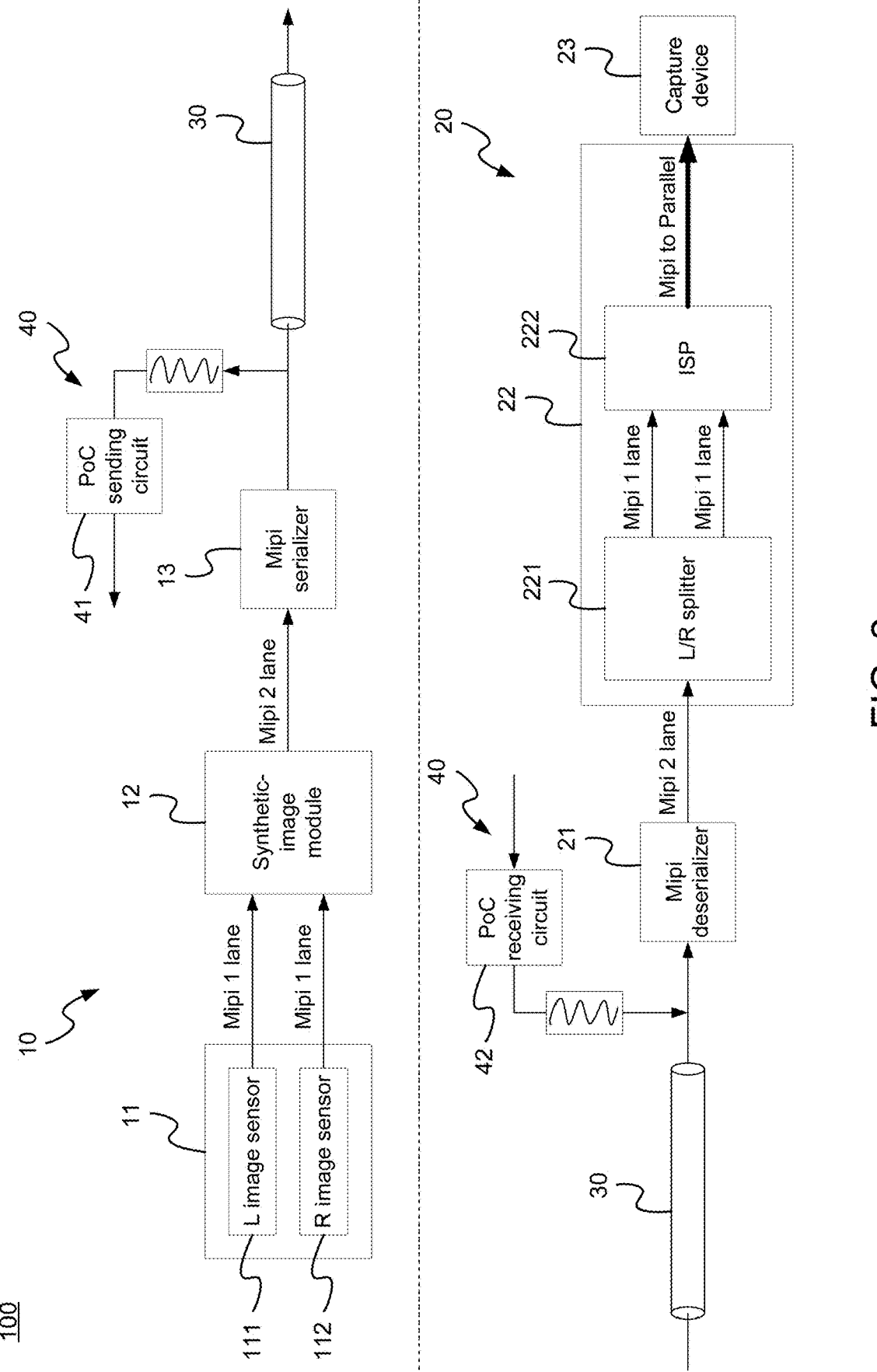
FIG. 2 is a schematic view showing the details of the structure.

Please refer to FIG. 1 and FIG. 2, which are a schematic view showing the structure of a preferred embodiment according to the present invention, and a schematic view showing the details of the structure. As shown in the figures, the present invention provides an apparatus of medical endoscope using MIPI serializer/deserializer 100, comprising a holding unit 10 and a capture unit 20. The holding unit 10 and the capture unit 20 are connected through a coaxial cable 30, and comprise a disposable image-capture module 11, a synthetic-image module 12, a MIPI serializer 13, a MIPI deserializer 21, a MIPI capture card 22, and a capture device 23.

The disposable image-capture module 11 is set at a front end of the holding unit and comprises a left image sensor 111 and a right image sensor 112. Therein, the front end of the holding unit 10 is a guide tube, which can extend into a body and has a length of at least 30 centimeters.

The synthetic-image module 12 is set in the holding unit 10 and connects to the disposable image-capture module 11.

The MIPI serializer 13 is set in the holding unit 10 and connects to the synthetic-image module 12.

The MIPI deserializer 21 is set in the capture unit 20 and connects to the MIPI serializer 13 through the coaxial cable 30, where the coaxial cable 30 has a length of 2~10 meters.

The MIPI capture card 22 is set in the capture unit 20 and connects to the MIPI deserializer 21.

The capture device 23 is set in the capture unit 20 and connects to the MIPI serializer 22.

The apparatus of medical endoscope using MIPI serializer/deserializer 100 further comprises a power-over-cable (PoC) module 40. The PoC module 40 comprises: a PoC sending circuit 41 set between the coaxial cable 30 and the MIPI deserializer 21; and a PoC receiving circuit 42 set between the MIPI serializer 13 and the coaxial cable 30.

Thus, a novel apparatus of medical endoscope using MIPI serializer/deserializer 100 is obtained.

On using the present invention, the disposable image-capture module 11 at the front end of the holding unit 10 extends into the body to use the left image sensor 111 to capture a set of left-image signals and the right image sensor 112 to capture a set of right-image signals. The set of left-image signals (L signals) and the set of right-image signals (R signals) are converted to be conformed to a MIPI single-channel (MIPI-1-lane) interface.

The synthetic-image module 12 receives the L signals and the R signals to form a set of synthesized image signals (L+R signals) containing all of the L signals and the R signals. After the set of synthesized image signals are converted to be conformed to a MIPI dual-channel (MIPI-2-lane) interface including Mipi PCLK and Mipi Data, the MIPI serializer 13 MIPI-serializes the set of synthesized image signals to output a flow of MIPI-serialized image data to the coaxial cable 30.

Figure 3:
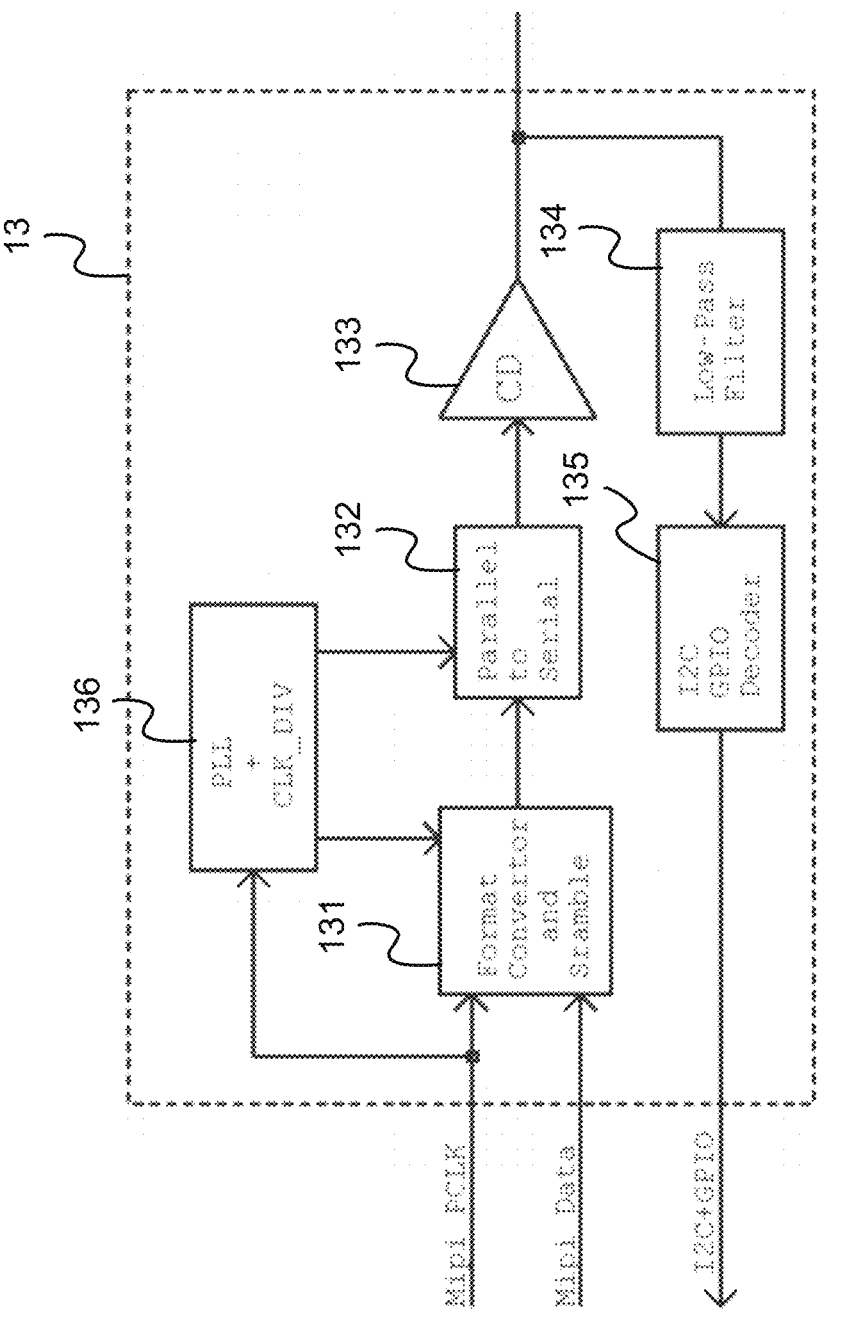
FIG. 3 is a schematic view of the internal structure of an MIPI serializer of the disclosure.

The internal structure of the MIPI serializer 13 is shown in FIG. 3, comprising: a Format Convertor and scramble 131 electrically connected to the synthetic-image module 12; a parallel to serial 132 electrically connected to the Format Convertor and scramble 131; a CD (Cable Driver) 133 electrically connected to the parallel to serial 132; a Low Pass filter 134 electrically connected to the CD 133; a I2C GPIO Decoder 135 electrically connected to the Low Pass filter 134; and a PLL and CLK_DIV 136 electrically connected to the synthetic-image module 12, the Format Convertor and scramble 131, and the parallel to serial 132. The synthetic image signal (Mipi PCLK and Mipi Data) enters the MIPI serializer 13, and the PLL and CLK_DIV 136 assists the Format Convertor and scramble 131 and the parallel to serial 132 in locking a frequency to be processed. The Convertor and scramble 131 converts the format of the synthetic image signal (Mipi PCLK and Mipi Data) and performs encryption thereon through scrambling. Next, the parallel to serial 132 converts parallel transmission to serial transmission, and then the CD 133 controls a transmission channel of the coaxial cable 30, allowing the flow of MIPI-serialized image data outputted by the parallel to serial 132 to be transmitted. The flow of MIPI-serialized image data is also inputted to the Low Pass filter 134 to filter out internal high-frequency video signals, allowing internal low-frequency I2C and GPIO to enter the I2C GPIO Decoder 135 for decoding and then sending out low-frequency I2C and GPIO control signal. In addition to data transmission, the apparatus of medical endoscope using MIPI serializer/deserializer 100 also uses a coaxial-cable power supplier 40 to supply power in a reverse direction. As shown in FIG. 1, the PoC sending circuit 41 is configured to send power over the coaxial cable 30; and the PoC receiving circuit 42 is configured to receive power from the coaxial cable 30 for supplying power to the disposable image-capture module 11 at the front end of the holding unit 10.

The MIPI deserializer 21 receives the flow of MIPI-serialized image data through the coaxial cable 30 to MIPI-deserialize the flow of MIPI-serialized image data to be restored and conformed to the MIPI-2-lane interface for outputting the set of synthesized image signals to the MIPI capture card 22. In a state-of-use as shown in FIG. 2, the MIPI capture card 22 has an L/R splitter 221, where the set of synthesized image signals is received to be split into two sets of image signals conformed to the MIPI-1-lane interface. Then, the two sets of image signals conformed to the MIPI-1-lane interface are outputted to an image signal processor (ISP) 222 to be converted into two sets of image signals conformed to the MIPI-2-lane interface. The two sets of image signals conformed to the MIPI-2-lane interface are processed through a MIPI-to-parallel data conversion to obtain parallel signals compatible to the capture device 23. At last, the capture device 23 converts the parallel signals into video-format data.

Figure 4:
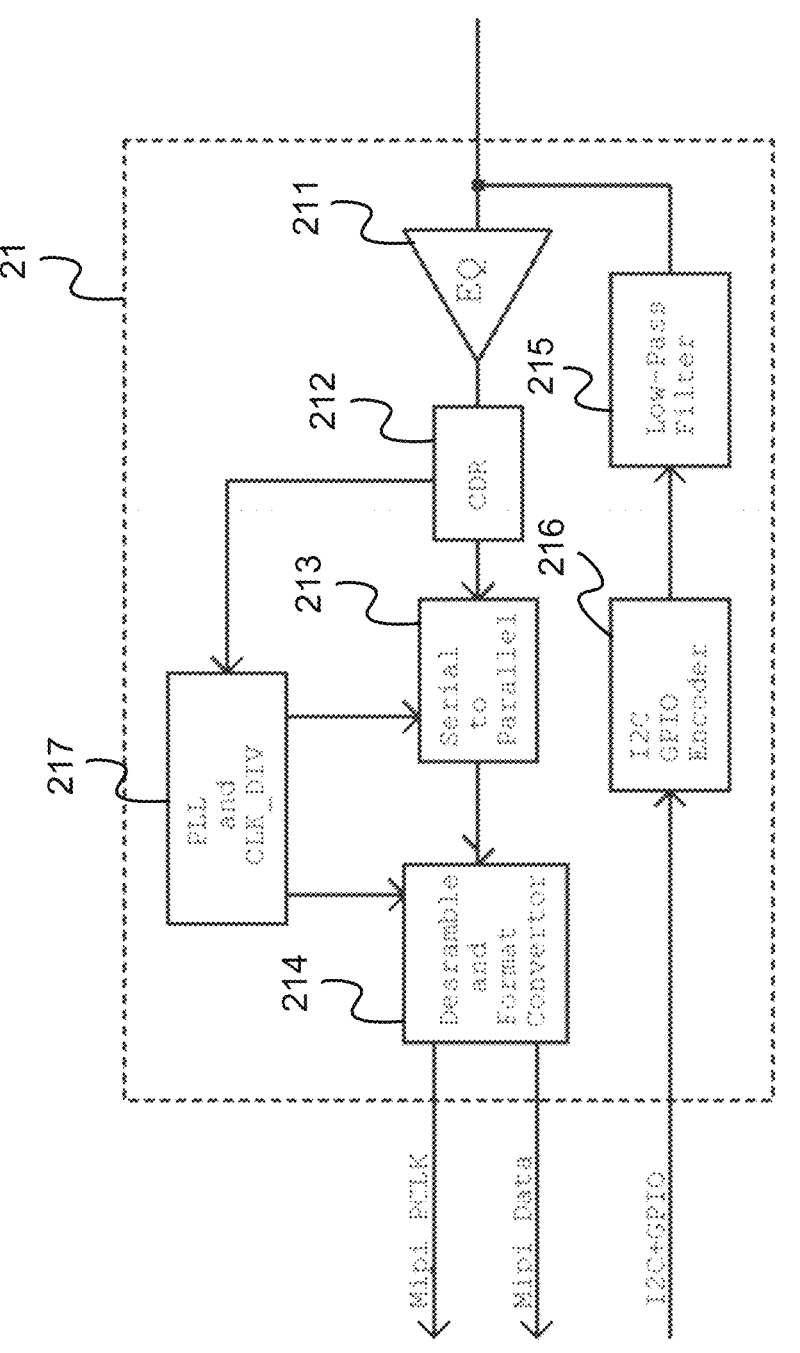
FIG. 4 is a schematic view of the internal structure of an MIPI deserializer of the disclosure.

The internal structure of the MIPI deserializer 21 is shown in FIG. 4, comprising: an EQ (Equalizer) 211 electrically connected to the MIPI serializer 13 through the coaxial cable 30; a CDR (Clock Data Recovery) 212 electrically connected to the EQ 211; a serial to parallel 213 electrically connected to the CDR 212; a Descramble and Format Convertor 214 electrically connected to the serial to parallel 213; a Low Pass filter 215 electrically connected to the EQ 211; a I2C GPIO Encoder 216 electrically connected to the Low Pass filter 215; and a PLL and CLK_DIV 217 electrically connected to the CDR 212, the serial to parallel 213, and the Descramble and Format Convertor 214. The PLL and CLK_DIV 217 assists the serial to parallel 213 and the Descramble and Format Convertor 214 in locking a frequency to be processed. After I2C+GPIO signal has entered the I2C GPIO Encoder 216 for encoding, the Low Pass filter 215 filters out high-frequency signal, allowing low-frequency I2C and GPIO control signal and the flow of MIPI-serialized image data to pass through the EQ 211 and then enter the CDR 212 to separate Clock and Data. Then, the serial to parallel 213 converts serial transmission to parallel transmission. Next, the Descramble and Format Convertor 214 performs descrambling and format conversion, reducing to a dual-channel interface of Mipi Data and Mipi of Mipi PCLK. Finally, the synthetic image signal is outputted to the MIPI capture card 22. Hence, the apparatus keeps the most expensive ISP and capture device at the back end and puts the disposable image-capture module, the synthetic-image module, and the MIPI serializer at the front end. After use, it is only necessary to discard the disposable image-capture module whose front end extends into human body. The remaining parts are reused. Thus, cost is effectively reduced to solve the shortcoming of high cost of the use of modern disposable endoscope.

To sum up, the present invention is an apparatus of medical endoscope using MIPI serializer/deserializer, where the most expensive ISP and capture device are kept at a back end and a disposable image-capture module, a synthetic-image module, and a MIPI serializer are put at a front end; after use, it is only necessary to discard the disposable image-capture module, which extends into human body at the front end, but the remaining parts are reused; and cost is thus effectively reduced to solve the shortcoming of high cost of the use of modern disposable endoscope. The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A medical endoscope comprising:

a holding unit comprising:

a multiple-use guide tube configured for extending into a body;

a single-use image-capture module arranged at a first end of the guide tube, wherein the single-use image-capture module comprises a left image sensor and a right image sensor, wherein said left image sensor and said right image sensor capture a set of left-image signals and a set of right-image signals, respectively, wherein said set of left-image signals and said set of right-image signals are each a single-channel signal;

a multiple-use synthetic-image module disposed in said holding unit, detachably connected to the single-use image-capture module, and receiving said single-channel sets of left-image signals and right-image signals to synthesize a set of dual-channel image signals containing all of said left-image signals and said right-image signals, the dual-channel image signals including differential signal PCLK and differential signal Data; and a multiple-use differential signal serializer disposed in said holding unit and connected to said synthetic-image module, wherein said differential signal serializer includes: a Format Convertor and scramble electrically connected to the synthetic-image module; a parallel to serial electrically connected to the Format Convertor and scramble; a CD (Cable Driver) electrically connected to the parallel to serial; a Low Pass filter electrically connected to the CD; a I2C GPIO Decoder electrically connected to the Low Pass filter; and a PLL and CLK_DIV electrically connected to the synthetic-image module, the Format Convertor and scramble and the parallel to serial; the synthetic image signal (differential signal PCLK and differential signal Data) entering the differential signal serializer, the PLL and CLK_DIV assisting the Format Convertor and scramble and the parallel to serial in locking a frequency to be processed, the Convertor and scramble converting a format of the synthetic image signal (differential signal PCLK and differential signal Data) and performing encryption thereon through scrambling, serializing the synthetic image signal by the parallel to serial, converting parallel transmission to serial transmission, controlling a transmission channel of the coaxial cable by the CD, allowing the flow of differential signal-serialized image data outputted by the parallel to serial to be transmitted, wherein the flow of differential signal-serialized image data is also inputted to the Low Pass filter to filter out internal high-frequency video signals, allowing internal low-frequency I2C and GPIO to enter the I2C GPIO Decoder for decoding and then sending out low-frequency I2C and GPIO control signal;

a multiple-use capture unit comprising:

a differential signal deserializer disposed in said capture unit and connected to said differential signal serializer to receive and deserialize said flow of serialized image data to be restored and conformed to said dual-channel signal to output said set of synthesized image signals; and a differential signal capture card disposed in said capture unit and connected to said differential signal deserializer, the differential signal capture card comprising an L/R splitter configured to receive the set of synthesized image signals to be split into two sets of image signals conformed to the single-channel signal, wherein the two sets of image signals conformed to the single-channel signal are outputted to an image signal processor (ISP) and converted into two sets of image signals conformed to the dual-channel signal, wherein the two sets of image signals conformed to the dual-channel signal are processed through a parallel data conversion to obtain parallel signals;

a multiple-use coaxial cable connecting the differential signal serializer of the holding unit and the differential signal deserializer of the capture unit; and a multiple-use power-over-cable (PoC) module comprising:

a PoC sending circuit disposed between the coaxial cable and the differential signal deserializer and configured to send power over the coaxial cable; and a PoC receiving circuit disposed between the differential signal serializer and the coaxial cable and configured to receive power from the coaxial cable to supply power to the single-use image-capture module at the first end of the holding unit.

2. The medical endoscope of claim 1, wherein said coaxial cable has a length of 2~10 meters.

3. The medical endoscope of claim 1, wherein said differential signal includes MIPI, LVDS, CML.

4. The medical endoscope of claim 1, wherein said differential signal serializer and said differential signal deserializer are constructed in an FPGA.

5. A medical endoscope comprising:

a holding unit comprising:

a multiple-use guide tube configured for extending into a body;

a single-use image-capture module arranged at a first end of the guide tube, wherein the single-use image-capture module comprises a left image sensor and a right image sensor, wherein said left image sensor and said right image sensor capture a set of left-image signals and a set of right-image signals, respectively, wherein said set of left-image signals and said set of right-image signals are each a single-channel signal;

a multiple-use synthetic-image module disposed in said holding unit, detachably connected to the single-use image-capture module, and receiving said single-channel sets of left-image signals and right-image signals to synthesize a set of dual-channel image signals containing all of said left-image signals and said right-image signals, the dual-channel image signals including differential signal PCLK and differential signal Data; and a multiple-use serializer disposed in said holding unit and connected to said synthetic-image module, wherein said serializer serializes said set of dual-channel synthesized image signals to output a flow of serialized image data;

a multiple-use capture unit comprising:

a differential signal deserializer disposed in said capture unit and connected to said differential signal serializer, wherein said differential signal deserializer includes: an EQ (Equalizer) electrically connected to the differential signal serializer through the coaxial cable; a CDR (Clock Data Recovery) electrically connected to the EQ; a serial to parallel electrically connected to the CDR; a Descramble and Format Convertor electrically connected to the serial to parallel; a Low Pass filter electrically connected to the EQ; a I2C GPIO Encoder electrically connected to the Low Pass filter; and a PLL and CLK_DIV electrically connected to the CDR, the serial to parallel, and the Descramble and Format Convertor; the PLL and CLK_DIV assisting the serial to parallel and the Descramble and Format Convertor in locking a frequency to be processed; I2C and GPIO signal entering the I2C GPIO Encoder for decoding, and then the Low Pass filter filtering out high-frequency signals, allowing low-frequency I2C and GPIO control signal and the flow of differential signal-serialized image data to pass through the EQ and then enter the CDR to separate Clock and Data, the serial to parallel converting serial transmission to parallel transmission, then the Descramble and Format Convertor performing descrambling and format conversion, reducing to a dual-channel interface of differential signal Data and differential signal PCLK, finally outputting the synthetic image signal;

a differential signal capture card disposed in said capture unit and connected to said differential signal deserializer, the differential signal capture card comprising an L/R splitter configured to receive the set of synthesized image signals to be split into two sets of image signals conformed to the single-channel signal, wherein the two sets of image signals conformed to the single-channel signal are outputted to an image signal processor (ISP) and converted into two sets of image signals conformed to the dual-channel signal, wherein the two sets of image signals conformed to the dual-channel signal are processed through a parallel data conversion to obtain parallel signals;

a multiple-use coaxial cable connecting the differential signal serializer of the holding unit and the differential signal deserializer of the capture unit; and a multiple-use power-over-cable (PoC) module comprising:

a PoC sending circuit disposed between the coaxial cable and the differential signal deserializer and configured to send power over the coaxial cable; and a PoC receiving circuit disposed between the differential signal serializer and the coaxial cable and configured to receive power from the coaxial cable to supply power to the single-use image-capture module at the first end of the holding unit.

6. The medical endoscope of claim 5, wherein said coaxial cable has a length of 2~10 meters.

7. The medical endoscope of claim 5, wherein said differential signal includes MIPI, LVDS, CML.

8. The medical endoscope of claim 5, wherein said differential signal serializer and said differential signal deserializer are constructed in an FPGA.

*  *  *  *  *